US008551030B2

(12) United States Patent
Jenkins, III (10) Patent No.: US 8,551,030 B2
(45) Date of Patent: Oct. 8, 2013

(54) DYNAMICALLY REACTIVE SPINAL SUPPORT SYSTEM

(75) Inventor: Arthur L. Jenkins, III, Greenwich, CT (US)

(73) Assignee: Pemaquid Holdings LLC, Greenwich, CT (US)

( * ) Notice: Subject to any disclaimer, the term of this patent is extended or adjusted under 35 U.S.C. 154(b) by 0 days.

(21) Appl. No.: 13/147,231

(22) PCT Filed: Nov. 2, 2010

(86) PCT No.: PCT/US2010/055043
§ 371 (c)(1),
(2), (4) Date: Aug. 1, 2011

(87) PCT Pub. No.: WO2011/056765
PCT Pub. Date: May 12, 2011

(65) Prior Publication Data
US 2011/0288459 A1     Nov. 24, 2011

Related U.S. Application Data

(60) Provisional application No. 61/257,793, filed on Nov. 3, 2009.

(51) Int. Cl.
*A61F 5/00* (2006.01)
(52) U.S. Cl.
USPC ............................................. 602/18; 602/19
(58) Field of Classification Search
USPC .......... 602/17–19, 5; 128/845–846, 857–858, 128/DIG. 23
See application file for complete search history.

(56) References Cited

U.S. PATENT DOCUMENTS

| 6,036,664 A * | 3/2000 | Martin et al. ..................... 602/5 |
| 2002/0113417 A1* | 8/2002 | Mattes ....................... 280/730.1 |
| 2004/0183283 A1* | 9/2004 | Buckman et al. .......... 280/730.1 |

* cited by examiner

*Primary Examiner* — Michael A. Brown
(74) *Attorney, Agent, or Firm* — Michael P. Pettit (57) ABSTRACT

A brace device for the spinal support of a wearer. The brace device comprises a plurality of component parts, with each component part being moveable relative to at least one other component part. Movement sensing means are provided, for monitoring the movement of the wearer and/or the movement of one component part relative to the at least one other component part with which it is moveable; the movement sensing means being able to generate output signals indicative of movement or in response to a change in movement. Movement resisting means are provided on component parts and these are operable to prohibit, restrict and/or resist movement of the component parts relative to other component parts. Control means in communication with the movement sensing means and the movement resisting means are programmed to interpret and/or analyze the output signals generated by the movement sensing means within predetermined parameters and/or criteria. Movement resisting means are activated, deactivated or dynamically controlled in response to signals received from the control means when it is determined that a movement or a change in movement requires partial or substantial immobilization of at least a portion of the spine of the wearer.

33 Claims, 3 Drawing Sheets

DYNAMICALLY REACTIVE SPINAL SUPPORT SYSTEM

BACKGROUND OF THE INVENTION

This invention relates to a brace device; typically for the provision of dynamic support to the back and/or neck of a wearer engaged in high-risk activities, or for dynamic immobilization and support of a patient suffering from a spinal injury. The brace device has ready applicability in protective or preventative applications, including incorporation in helmets and padding used by racing car drivers, football players, and military personnel; and in medical applications, including cervical collars and other spinal bracing for trauma victims after an accident or injury.

The invention addresses the need to minimize abnormal movement of the head, neck, back and/or spine during an impact or collision, or other injury-causing sudden change in movement; providing rigidity that restricts the potentially injury-causing movements from being subjected to the spine, whether from the original impact or change in movement and/or upon subsequent recoil.

SUMMARY OF THE INVENTION

According to a first aspect of the invention there is provided a brace device for the spinal support of a wearer, the brace device comprising: a plurality of component parts, each component part being moveable relative to at least one other component part; movement sensing means, for monitoring the movement of at least one component part relative to at least one other component part with which it is moveable, the movement sensing means generating one or more output signals indicative of said movement or in response to a change in movement; movement resisting means, provided on one or more of said component parts and operable to prohibit, restrict and/or resist movement of at least one component part relative to at least one other component part; and control means in communication with the movement sensing means and the movement resisting means, the control means being programmed to interpret and/or analyze the said one or more output signals generated by said movement sensing means within predetermined parameters and/or criteria; wherein one or more of the movement resisting means are dynamically controlled in response to one or more signals being received from the control means when the control means determines a movement or change in movement requires partial or substantial immobilization of at least a portion of the spine of the wearer.

Typically the brace device is utilized in the mitigation or prevention of injuries to a wearer participating in high risk activities. Such activities typically involve a risk of significant impact to the body, back or head of the wearer, or to the vehicle or equipment with which the wearer may be associated.

Preferably, the brace device is arranged to have one or more component parts, alone or in combination with other component parts, substantially or partially encircle and/or lie adjacent one or more portions of the spine of the wearer; typically the neck, and more particularly, around the cervical and thoracic portion of the spinal column of the wearer. The component parts are typically plates. Preferably, the brace device is comprised of combined neck and chest collar portions.

Preferably, the movement sensing means and the movement resisting means are adapted to sense and resist linear, shear and rotational movement.

The movement sensing means may include one or more micro electro-mechanical accelerometers, gyroscopes, force-transducers, pressure sensors and/or strain gauges.

Preferably, the movement sensing means are adapted to sense the rate of change in velocity (acceleration/deceleration) and/or a change in inclination (pitch and/or yaw). The movement sensing means typically include an accelerometer and/or gyroscope, capable of detecting movement changes in three dimensions (triple-axis). Preferably, the movement sensing devices are micro electro-mechanical systems.

The movement sensing means may include the airbag deployment system and/or the dynamic stability control system of the vehicle in which the wearer is travelling.

Typically, the control means is an electronic microprocessor, connected by wire or connected wirelessly to the movement sensing means and the movement resisting means. Typically, the connections are flexible electrical conducting wires.

Typically, the component parts are operable to articulate, relative to one another, at one or more interfaces defined by the movement resisting means, whereby a tendency for a motion of one component part relative to another component part is prohibited, restricted and/or resisted. Alternatively, in certain situations, for example after an impact is subjected on a wearer, a tendency for the interface to remain in a statically abnormal immobilization configuration, or to urge further secondary movement between the component parts into a secondary configuration, may be permanently or temporarily assisted in order to prevent or mitigate further injury from rebound or recoil movement of the head and/or body of the wearer after an impact or other injurious event.

Typically, the component parts are adapted from moveable overlapping plates, preferably manufactured from a breathable fabric (for comfort), that is adapted to allow relatively free movement of the neck and head under normal circumstances, but provides immediate immobilization at the initiation of abnormal head, neck or spinal movement. The movement resisting means are typically located in the region of possible overlap.

Typically, the brace device may comprise means for generating a wireless distress signal, operable to notify emergency crews after the activation of the device.

One or more component parts may be tethered or otherwise connected to a helmet worn by the wearer. The helmet may itself be formed of one or more parts, at least one of which may act as a component part relative to the component parts of the brace device.

According to a second aspect of the invention there is provided a brace device for the spinal support of a wearer, the brace device comprising: a flexible smart fabric, operable to partially or substantially enclose and/or lie adjacent to one or more portions of the spine of the wearer; movement sensing means, for monitoring the movement of at least one location on the smart fabric relative to one or more other locations on the smart fabric and/or other portions of the brace device, the movement sensing means generating one or more output signals indicative of said movement or in response to a change in movement; fabric hardening means, operable to partially or substantially harden one or more regions of the smart fabric upon application of a stimulus, thereby to prohibit, restrict and/or resist movement of one or more portions of the spine of the wearer; and control means in communication with the movement sensing means and the hardening means, the control means being programmed to interpret and/or analyze the said one or more output signals generated by said movement sensing means within predetermined parameters and/or criteria; wherein one or more regions of the flexible fabric is dynamically controlled in response to one or more signals being received from the control means when the control means determines a movement or change in movement requires partial or substantial immobilization of at least a portion of the spine of the wearer.

The smart fabric may be tethered or otherwise connected to a helmet worn by the wearer. The helmet may itself incorporate a smart fabric which may respond independently or in response to one or more signals being received from the control means.

A brace device for the support of a wearer, the brace device comprising: a flexible smart fabric, operable to partially or substantially enclose and/or lie adjacent to one or more portions of the muscular-skeletal system of the wearer; movement sensing means, for monitoring the movement of at least one location on the smart fabric relative to one or more other locations on the smart fabric and/or other portions of the brace device, the movement sensing means generating one or more output signals indicative of said movement or in response to a change in movement; fabric hardening means, operable to partially or substantially harden one or more regions of the smart fabric upon application of a stimulus, thereby to prohibit, restrict and/or resist movement of one or more portions of the muscular-skeletal system of the wearer; and control means in communication with the movement sensing means and the hardening means, the control means being programmed to interpret and/or analyze the said one or more output signals generated by said movement sensing means within predetermined parameters and/or criteria; wherein one or more regions of the flexible fabric is dynamically controlled in response to one or more signals being received from the control means when the control means determines a movement or change in movement requires support of the muscular-skeletal system of the wearer.

Preferably, the brace device of any aspect of the invention includes additional sensors for monitoring the physical condition or the wearer, including the heart rate, body temperature, blood pressure and the presence and/or location of bleeding.

Preferably, the dynamic control is operable to reactivate and/or vary the duration and/or force applied by the movement resisting means, or the fabric hardening means, in prohibiting, restricting and/or resisting movement.

The illustrations are intended to provide a general understanding of the concepts described and the structure of various embodiments, and they are not intended to serve as a complete description of all the elements and features of methods and systems that might make use of the structures or concepts described herein. Many other embodiments will be apparent to those of skill in the art upon reviewing the description. Other embodiments may be utilized and derived therefrom, such that structural and logical substitutions and changes may be made without departing from the scope of this disclosure. It should also be appreciated that the figures are merely representational, and are not be drawn to scale and certain proportions thereof may be exaggerated, while others may be minimized. Accordingly, the specification and drawings, together with any examples, are to be regarded in an illustrative rather than a restrictive sense and the specific form and arrangement of the features shown and described are not to be understood or interpreted as limiting on the invention.

DESCRIPTION OF EMBODIMENTS

Figure 1:
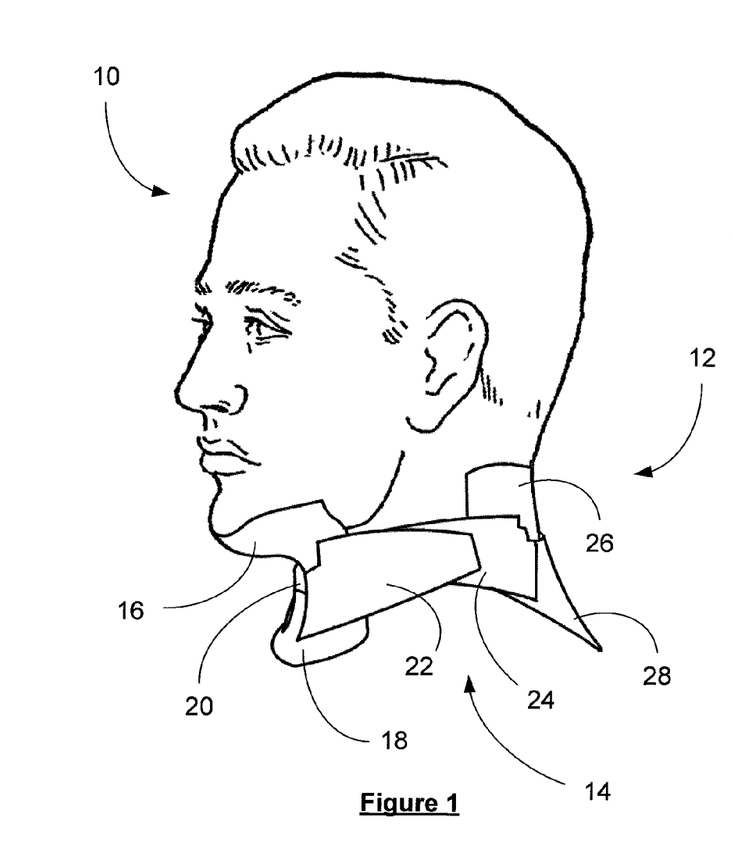
FIG. 1 shows the head and neck of a wearer fitted with a cervical collar brace device according to a first embodiment of the present invention, in a normal, free movement position.

In FIG. 1, a wearer's head 10 is depicted, with a simple electromagnetically activated cervical collar brace device 12 located around his neck 14.

The cervical collar 12 encircles the neck 14 of the wearer and is comprised of several moveable and overlapping component parts; including a central anterior superior part 16, a central anterior inferior part 18, a central anterior middle part 20, a left anterior lateral (visible) and a right anterior lateral part 22, a left posterior inferior (visible) and a right posterior inferior part 24, a central posterior inferior part 26 and a central posterior superior part 28.

It should be apparent, in the embodiment depicted in FIG. 1, that certain component parts are moveable relative to one or more other component parts in rotational, shear and/or linear orientations. For example, the interface between the left anterior lateral part 22 and the left posterior inferior) part 24 is rotatable and the combination of the two pieces may be extended or contracted. Together, the numerous component parts of the cervical collar brace device 12 allow relatively free movement of the head and neck under normal circumstances. However, immediate immobilization is initiated in the event of an abnormal neck movement being detected. All of the pieces are linked together, and the tethers that connect them will prevent the pieces from being unable to function when needed to limit movement.

Although a limited number of component parts are illustrated in FIG. 1, it should be readily apparent that the invention contemplates that more or less component parts could be incorporated in the brace device 12; more parts increasing complexity, but also affording increased flexibility of movement. The number, shape and size of the parts may be varied to accommodate differences in the size, shape, and purpose of the brace device. The component parts typically overlap over articulated interfaces; similar to the manner fish scales and ancient armor plating enable movement.

Figure 2:
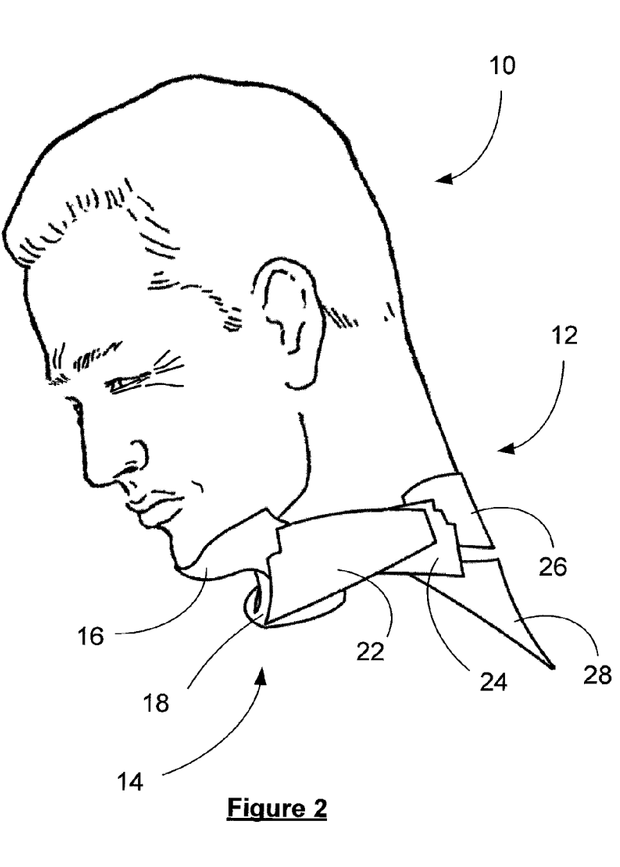
FIG. 2 shows the wearer and collar of FIG. 1, wherein the head and neck have been extended forward to a potentially abnormal position following an impact being subjected to the wearer, and the collar brace device has been engaged to restrict movement of the head and neck.

In FIG. 2, the wearer's head 10 has been subjected to an impact force directed substantially from in front of his original position. The wearer may have been moving forward and then stopped suddenly (such as in a collision), or he may have been pushed backwards suddenly (such as in a tackle in football). In either event, the resultant movement causes an improper and abnormal extension of the neck at the rear, and an accompanying compression of the vertebrae at the front, as the head is propelled forward.

The impact has subjected considerable force on the wearer 10 and this has caused the central anterior superior part 16 (the piece below the chin) to move down toward the central anterior inferior part (the piece above the breastbone) 18. The left anterior lateral part 22 and left posterior inferior part 24 have also been caused to contract and rotate relative to one another and the central posterior inferior part 26 and central posterior superior part 28 have moved apart. Following impact, it is possible that the recoil of the head and/or body could be thrown backwards; potentially causing additional injury to the head and spine, especially as the wearer may have lost consciousness or have a reduced muscular response to resist the secondary movement. In practice, such recoil movements may well cause a more harmful injury than that inflicted from the initial impact; or the original injury may be further compounded or exacerbated by the secondary movements. Indeed, in certain applications (such as "American" football) the subsequent swinging of the heavier, helmeted head can prove more injurious to the athlete than the initial inline impact.

Consequently, the present invention attempts to minimize the severity of such injuries, by prohibiting, resisting and/or restricting movement between component parts, and thereby dynamically immobilizing the head and/or neck during the impact, and possible after recoil. Additionally, depending on the circumstances, the immobilized configuration may be held temporarily or until emergency medical care is available; or alternatively, subsequent secondary movements may also be resisted or restricted as the collar dynamically adjusts to a secondary modified immobilization configuration.

The cervical collar brace device 12 is typically intended to be worn as part of the safety equipment associated with high-risk activities undertaken by individuals in sports (e.g. race car drivers and athletes such as football players), entertainment (stunt persons) and military, police or security personnel. In circumstances where a helmet is worn by the wearer of the brace device, one or more of the component parts may be tethered or otherwise connected to the helmet. Moreover, the helmet may itself be formed of one or more parts, at least one of which may itself act as a component part relative to the component parts of the brace device; thereby providing additional stability between the brace device and helmet, and consequently contributing supplemental support between the head and neck. Where the user is seated, all or part of the brace device could be provided on the seat.

Figure 3:
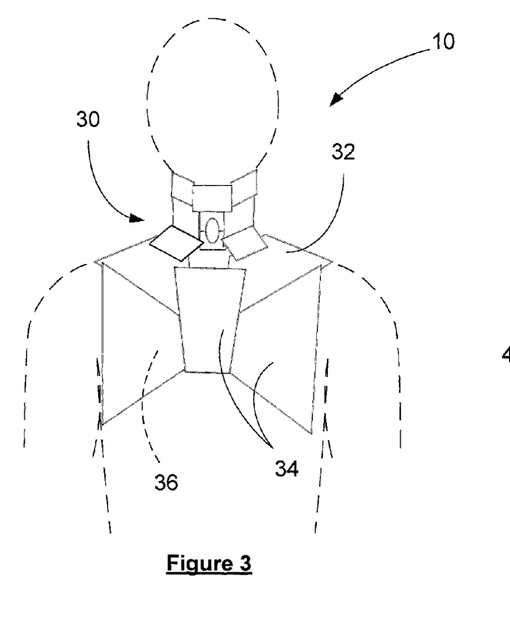
FIG. 3 shows a simplified drawing of an alternate embodiment of the brace device of the present invention, wherein the brace device comprises component parts located around the cervical portion of the spine, with additional support being provided from component parts provided on the shoulders, chest and upper back of the wearer.

FIG. 3 shows an alternate embodiment of the brace device 12 depicted in FIGS. 1 and 2, where the brace device comprises component parts 30 around the cervical portion of the spine, with additional support being provided from component parts provided on the shoulders 32, chest 34 and upper back 36 of the wearer 10.

It should be readily apparent that the responses described above in relation to a frontal impact can equally be appropriately directed to side, rear and combination impacts or other sudden changes in movement.

The brace device of the present invention may comprise internal and/or external movement sensing means for determining any external forces being applied to the wearer 10. This force will manifest itself in two ways: causing the head to be pushed in one direction (angular movement) as well as a downward (translational) movement on the head. Typically the movement sensing means are operated continuously during any activity potentially requiring support from the brace device 12. Movement sensing means include, but are not necessarily limited to, accelerometers, gyroscopes, force-transducers, pressure sensors, strain gauges and the like. Generally the brace devices will utilize accelerometers and gyroscopes; although the device may incorporate any of these or other sensing devices or products.

Gyroscopes can detect variations in the inclination or the brace device, namely pitch and yaw. Accelerometers monitor the magnitude and direction of acceleration (the rate of change in velocity) as a one, two, or three dimensional vector quantity that can detect changes in orientation and the application of shocks. Preferably, the accelerometers utilized are three dimensional (triple-axis) detecting accelerometers, but combinations of these sensors can achieve similar goals. As with presently available airbag deployment mechanisms, accelerometers may be used to detect the rapid negative acceleration (deceleration) of the vehicle and the brace device wearer and thereby determine when a collision has occurred, and provide signals and/or data relating to the severity of the impact.

These movement sensing means may be deployed externally, being mounted on one or more of the component parts, such as on a chest piece, or carried independently by the wearer 10 (such as in clothing or on a tool, sporting equipment or other appropriate device), or be linked to the vehicle or device to which the wearer is active or associated (whether a car, boat, airplane, bicycle, hand-glider or any other "vehicle" with which the wearer is associated). For example, a wearer in a vehicle may have a brace device 12 that is in communication with the vehicle's airbag sensors and/or the dynamic stability control sensors (controlling vehicle handling in response to cornering and braking forces etc); where the brace device is activated completely or partially upon certain of the vehicle systems experiencing one or more predetermined conditions. The movement sensing means may also be deployed internally within the brace device; for example, on one or more of the component parts. Modern accelerometers, gyroscopes and other sensing devices are often very small micro electro-mechanical systems (as evidenced by their use in many handheld consumer electronic devices), which facilitates such usage.

Typically the accelerometer and/or gyroscopes will provide a three-dimensional vector that can be incorporated in the determination of an appropriate reaction in the partial or complete activation of immobilization of the brace device 12.

The movement sensing means enable the detection of forces that potentially inflict supra-physiological strains on the wearer. Upon receipt of one or more output signals generated and communicated to a microprocessor control means by the movement sensing means, the microprocessor control means analyzes and interprets the received signals and determines, in accordance with preprogrammed parameters and criteria, whether the output signals are indicative of potentially injury inflicting movement or change in movement.

In the event that the microprocessor determines that the movement of one or more component parts of the brace device should be prohibited, restricted or resisted, the microprocessor activates movement resisting means, located on one or more of the component parts. These movement resisting means are operable to prohibit and/or resist movement of the component parts relative to at least one other component part. The movement resisting means may be activated, deactivated or dynamically controlled when the control means determines a movement requires support, or a change in support, of the spine. The movement resisting means are typically electrically activated micro-spot electromagnetic lock assemblies 40, as shown in FIG. 4, comprising a catch-plate 42, having conductive spots (flat spots), and an electromagnetic lock device 44, having double concentric electrical elements (target spot).

The microprocessor may be programmed with specific parameters and criteria that are refined and nuanced for the particular needs of the wearer and/or activity. The typical algorithm for calculation of net force vectors follows the Pythagorean Theorem: if the acceleration in three-dimensions has a value of x for the vertical (up-down) axis, y for the horizontal (left-right) axis, and z for the horizontal (forward-back) axis, then the formula for net acceleration (n) is expressed as $n^2=x^2+y^2+z^2$. The absolute value of a net acceleration that exceeds certain parameters, and/or certain limits on the individual parameters, will trigger the device to immobilize. There may also be individual customized settings for the duration and strength of the immobilization force applied. In general, vertical translation is less well tolerated than lateral movements, so these parameters may typically have lower thresholds for activation.

The type of locking mechanism appropriate for immobilization of the brace devices may vary across different needs and applications. There can, for example, be mechanical immobilization, such as an electrostatically activated form of hook-and-eye fabric (like Velcro™); where in the resting phase the fabric can move smoothly, but upon activation of an appropriate electrical, mechanical, chemical or magnetic signal the fabric is caused to become "sticky". Chemical immobilization through chemical bonds could also be applied as a locking mechanism, or other alternative types of physical locking mechanisms. However, in FIGS. 5a and 5b a simple system for immobilization is described, involving the use of electromagnetic locks.

Figure 4:
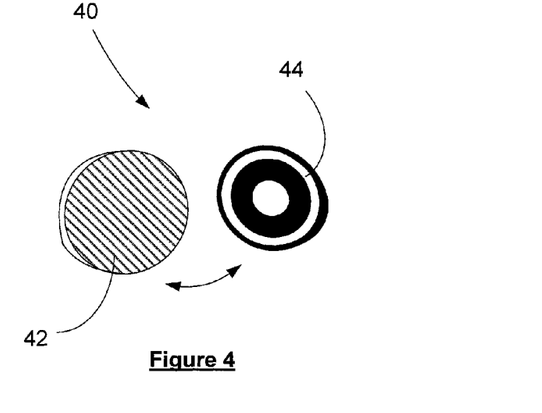
FIG. 4 shows an electromagnetic locking assembly, with corresponding engageable catch-plate and electromagnet components.
Figure 5A:
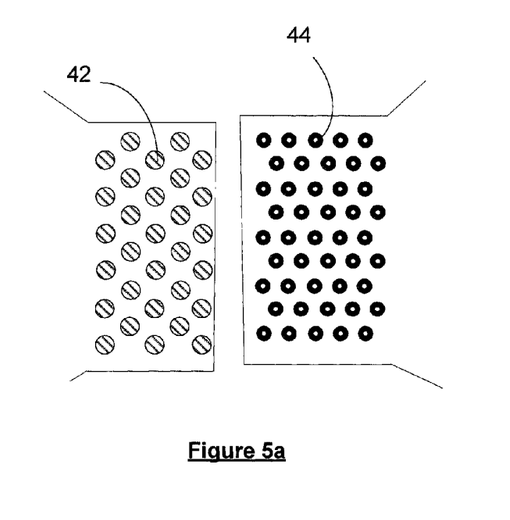
FIGS. 5a and 5b show the electromagnetic locking assemblies of FIG. 4, located on the mating (overlapping) portions of adjacent component parts.

FIG. 5a shows several small electromagnetic lock assemblies 40 of FIG. 4, affixed to partially or completely overlapping portions of the component parts of the brace device 12. One component part comprises an interface area of catch-plates 42 and the other has a complementary area of electromagnetic lock devices 44. The complementary areas are provided in areas that facilitate activation of a locked brace device interface in normal and anticipated abnormal positions.

The two sets are laid out so that the maximum number of productive contacts will be made, and no short-circuits exist. In the preferred embodiment, each interface is charged with a 4 volt, 0.015 amp continuous draw that will divide the equivalent force of 4 lbs force across the active electromagnetic lock assemblies. Consequently, a hexagonal pattern is formed, such that the size of the flat spots are typically 25% larger in diameter than the target spots, the target spots are separated by the diameter of the flat spots, and the flat spots spaced apart at a distance calculated at 110% of the target diameter.

The initial dimension chosen for the target spots is an approximate outer radius of 0.5 mm (outer contact is 0.05 mm thick, insulator is 0.2 mm thick and the inner spot radius is 0.2 mm). This configuration substantially prevents any target spot from coming into contact with more than one flat spot. Each target spot is consequently approximately 1.0 mm in diameter, spaced 2.25 mm apart (center to center).

Each flat spot is approximately 1.25 mm in diameter, spaced approximately 1.1 mm apart.

On a 1 cm overlap that is 3 cm long, this will result in a grid of 3×9 target spots and a grid of 4×11 flat spots. While this may not be a linear matching, the variable spacing allows for there to be a few target spots in direct contact with flat spots at all times, without needing to be realigned first.

Figure 5B:
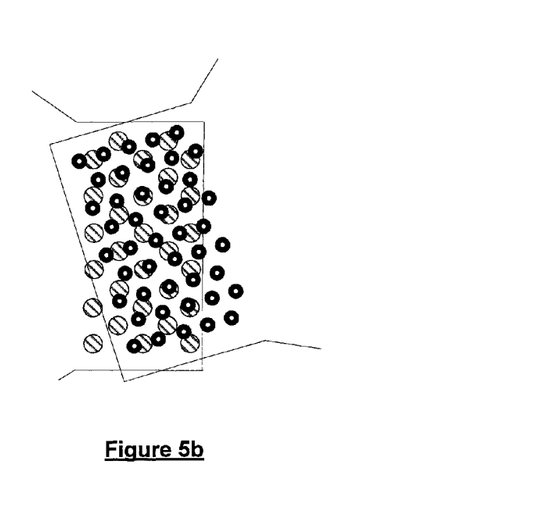

FIG. 5b shows two complementary portions of the component parts of the brace device, rotated and linearly moved in an overlapping configuration that enables immediate immobilization or resisted movement.

A power source, such as a battery located in the chest plate component part, or connected externally to the brace device 12, maintains an electric charge across the electromagnetic lock assemblies 40 while activated. The initial discharge, which needs to be a higher current delivered to maintain a stronger force for immobilization, may be delivered by a capacitor charged by the battery, or there may be a battery that has a high enough discharge rate to achieve this force applied across the multiple electromagnetic locks simultaneously. Once activated, and once the initial time period of maximum immobilization passes (as programmed), the force applied may reduce to a lower force once the collision event has ended.

In a collision event, for example, this charge may be held until emergency services arrive. The brace device may then be deactivated or connected to a supplemental power source. The initial charge applied is typically a higher rating in order to apply maximum holding force to the interfaces holding the component parts. However, the charge may then be lowered to maintain the position after a predetermined time, for example after the first minute has passed since activation. This reduction in supplied charge allows for maximum battery life, while still maintaining sufficient holding force to immobilize spine of the wearer. This prevents movement of the neck or back from the position attained at the time of injury, minimizing the chance of subsequent movement-related injury, but allows emergency medical service personnel (EMS) then to deactivate the brace device, reposition the head if necessary under controlled supervision and re-establish a preferred immobilization position.

Alternatively, in a temporary stress situation, for example a racing driver or pilot being subjected to excess G-forces, the brace device 12 may provide temporary bracing for the duration of the stress inducing situation (cornering, braking etc). In such circumstances, the activation of the brace device, and accompanying provision of applicable charge and holding force to the component parts, is more dynamic and changeable.

Insulated flexible wires attach the individual component parts to each other to carry the electric current, as well as to carry the output signals generated by movement sensors to the microprocessor and the electronic signals to the movement resisting means. The brace device could also incorporate a wireless distress signal generating mechanism, operable to notify emergency crews in the event of the deployment of the device. There are multiple component part interfaces, each of which is separately charged from the battery; consequently, the brace device may also be provided with an alarm mechanism to provide a warning sound to alert the wearer if any contacting interfaces are dysfunctional.

In an alternative embodiment, the catch-plate side of the component part may be provided only with a smooth flat conductive surface, with all target spots contacting this single conductor. In another alternative embodiment, the hexagonal shaped pattern of the flat spots is located with insulated spaces calculated at approximately the thickness of inner spot of the electromagnetic lock, to prevent multiple contacts.

Commercially available electromagnetic lock assembles of the kind described above exhibit a holding force capable of holding approximately 25 lbs (11.3 kg), using operating voltages of 24VDC, 24VAC or 120VAC/60Hz. This unit will have a continuous current draw of 0.015 Amps, (regardless of whether the current used is direct or alternating, and regardless of the voltage applied). The resistance to shear forces of this assembly is such that it requires a much greater orthogonal force to displace a force applied.

In the preferred embodiment, the component parts would be manufactured as individual plates, having edges with slide guards that prevent them from sliding too far in any one direction, while maintaining the electromagnetic lock assemblies in generally layered apposition. The plates are preferably formed from injected molded plastic, but polycarbonate, Kevlar™, nano-machined substances, metals and other woven or machined materials can be substituted based on the needs and application of the device (military applications may be coated or made with Kevlar to resist bullets, shrapnel, or knife wounds) in order to provide some flexing, and thereby further reducing applied forces in the event of severe physical stresses.

In addition, there would be sufficient overlap between the interfacing plates to allow for a full range of motion, when not activated, in all cardinal ranges of motion (flexion, extension, left and right lateral bending, and left and right rotation), while still having a sufficient number of micro-spots in potential contact to apply an adequate force capable of preventing sliding. As the force required to prevent sliding of the plates would be a substantially orthogonally applied shear to the electromagnetic force, a small electromagnetic force is sufficient to prevent all but the most severe of physical forces from deforming the brace device 12 once activated.

The component part plates' movement is preferably limited so that the edges are not able to slide to the extent that the micro-spots cease to be in contact with each other. This will typically be achieved by having small angled "stops" that prevent too much overlap, and by providing a nylon safety strap on each overlap to prevent complete separation.

Figure 6:
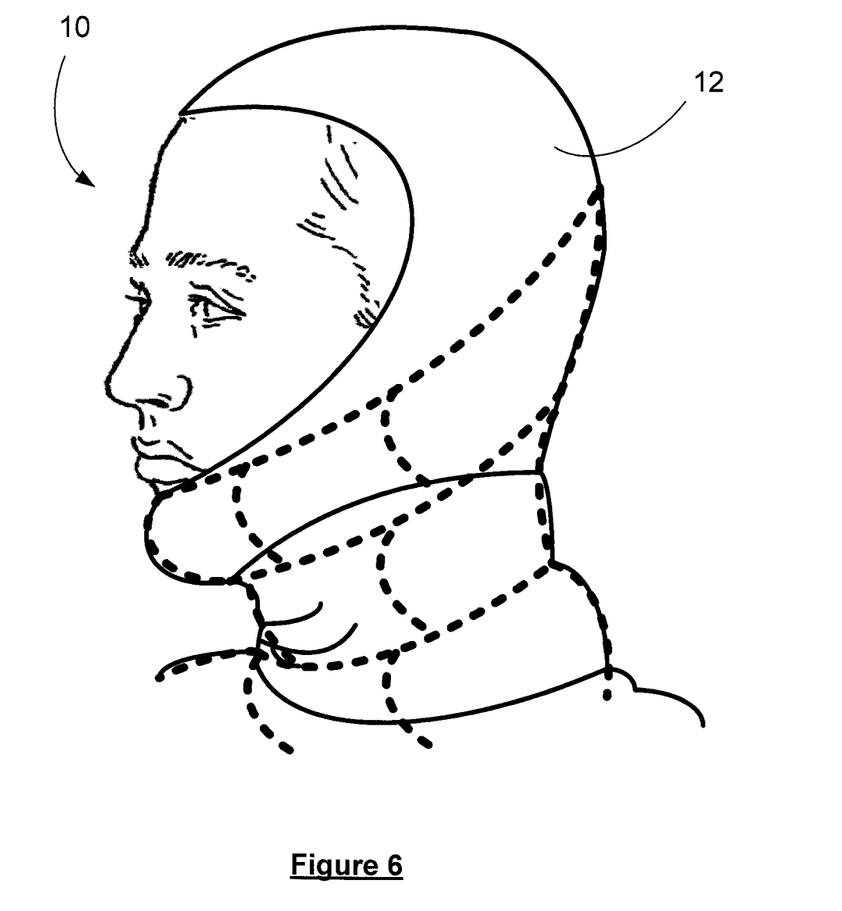
FIG. 6 shows a simplified drawing of an alternative embodiment of the invention adapted to be worn as a balaclava in high-risk activities.

FIG. 6 shows an alternative embodiment of the brace device 12, where the brace device would pull on over the head of a wearer 10 (much like a turtleneck and balaclava, with no sleeves) with component part plates extending down into the chest and back area. The collar would extend up over the lower jaw and behind the inion (bony prominence of occipital bone at the back of the skull just above the neck) to provide full immobilization.

A third embodiment of the invention utilizes "smart materials" or "intelligent textiles" in the brace device. Although, such fabrics are sometimes distinguished in the art (the former sensing environmental conditions or stimuli, and the latter considered capable of also reacting to the conditions or stimuli), no such distinction is made in this specification. The term "smart fabric" is herein used to encompass both possibilities generally. Smart fabrics typically utilize nanotechnology and are generally soft and flexible in normal circumstances, but are able to harden almost instantaneously when subjected to an impact or other external stimulus.

An example of an innovative early electro-conductive smart fabric is ElekTex, developed by Eleksen Ltd, a British company. This product uses technology that sandwiches an electrically conductive, proprietary, knitted textile between carbon-impregnated knitted nylon layers, which in turn are covered with an outer layer similar to woven nylon. The resulting product is flexible and "touch sensitive;" being capable of sensing the position of a touch on the surface, as well as differentiating the intensity of the pressure applied. Another example is the Dow Corning Active Protection System; which is soft, flexible and breathable in normal conditions, but hardens almost instantly upon receiving an impact (and then returns to the flexible state when the impacting force is removed). The Scandinavian Research organization SINTEF has also developed a generally soft and flexible material called "d3o", which uses intelligent molecules that flow freely until subjected to pressure, whereupon they instantly lock to harden and absorb/distribute the impacting force. This product is known to be used in helmet lining. Additionally, United States patent application 2010/0007240 A1 (inventors Kornbluh, et al) discloses "meta-materials" that are controllable and capable of dynamic activation through various means. That patent application provides that the material is sufficiently flexible that clothing may be formed from it; and the material may be used for casts and braces which are switchable from soft/flexible to hard/stiff, and which are re-adjustable for rest periods or for changes in support required in healing.

It will be appreciated from the above, that hardening of the smart material in response to a direct impact, or when required for a change in positioning or sizing, is known. However, hardening of the smart material (without the material necessarily being subjected to a simultaneous direct impact) in response to a movement or a change in movement determined to be potentially injurious is not contemplated in the art. The present invention envisages use of garments or other suitable products utilizing smart fabrics that form the brace device, or form part of a brace device. The material could be activated by application of an appropriate stimulus, such as a current, a change in current, or the stopping of the current; such that the smart fabric is caused to "freeze" in its current state, position or shape, or which demonstrates variable rigidity to provide resistance to movement. The tensile properties within one or more regions of the fabric being altered in response to the stimulus, which activates, deactivates or dynamically controls fabric hardening means; thereby partially or substantially hardening these regions. The stimulus and/or hardening means may be thermal, chemical, mechanical, electrical, magnetic or from another appropriate source. For example, the above mentioned products could readily be caused to harden by mimicking, in response to the movement or change in movement, the stimulus and reaction resulting from a directly impacting event.

The present invention also contemplates movement sensing means being provided on one or more locations on the smart fabric and/or other elements of the brace device (if applicable). The smart fabric may additionally include other sensors. For example, researchers have found that molecules of a material that reacts with human serum albumin can be added (coated on) to the fibers of the fabric; which molecules detect the presence, location and intensity of bleeding (on application of an electric current through the fibers and measuring the changing conductivity across the fabric). Other sensors may also be included on the brace device, being a capable of monitoring the physical condition or heath of the wearer, including the heart rate, body temperature and blood pressure etc. All of this information may be communicated directly or wirelessly to emergency personnel that respond to an injury inflicted on the brace device wearer in order to assist them in the appropriate care and treatment.

It will be appreciated that the embodiments described in this specification relate to the support of the spine of a wearer in response to conditions that potentially inflict physiological stresses and strains. This invention contemplates that appropriate modifications to the brace device could readily be made to control or prevent unwanted or abnormal movement in other muscular-skeletal regions of the body, such as hinged joints, for use in medical rehabilitation, physical training, or other situations where the potential for injury is high.

Reference is made in this specification to the application of microprocessors that may be used in accordance with the present invention and as applied in some example embodiments. It should be appreciated that the microprocessors may operate as a standalone device or may be connected (e.g., networked) to other microprocessors, computers or devices. In a networked deployment, the microprocessors may operate in the capacity of a server or a client machine in a server-client network environment, or as a peer machine in a peer-to-peer (or distributed) network environment. The microprocessor may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while a single microprocessor may be described, a single microprocessor shall also be taken to include any collection of microprocessors that individually or jointly execute a set (or multiple sets) of instructions to perform any one or more of the functions described in this specification.

Machine-readable media may be provided, on which is stored one or more sets of instructions (e.g., software, firmware, or a combination thereof) embodying any one or more of the functions described in this specification. The instructions may also reside, completely or at least partially, within the main memory, the static memory, and/or within the processor during execution thereof by the computer system. The instructions may further be transmitted or received over a network via the network interface device.

In example embodiments, a microprocessor may be configured to perform certain operations. In other embodiments, the device may include dedicated circuitry or logic that is permanently configured (e.g., within a special-purpose processor) to perform certain operations. It may also comprise programmable logic or circuitry (e.g., as encompassed within a general-purpose processor or other programmable processor) that is temporarily configured by software to perform certain operations. It will be appreciated that the decision to implement the device mechanically, in the dedicated and permanently configured circuitry, or in temporarily configured circuitry (e.g. configured by software) may be driven by cost and time considerations. Accordingly, the term "microprocessor" should be understood to encompass a tangible entity, be that an entity that is physically constructed, permanently configured (e.g., hardwired) or temporarily configured (e.g., programmed) to operate in a certain manner and/or to perform certain operations described herein.

The invention claimed is:

1. A brace device for the spinal support of a wearer, the brace device comprising:
   a plurality of component parts, each component part being moveable relative to at least one other component part;
   movement sensing means, for monitoring the movement of at least one component part relative to at least one other component part with which it is moveable, the movement sensing means generating one or more output signals indicative of said movement or in response to a change in movement;
   movement resisting means, provided on one or more of said component parts and operable to prohibit, restrict and/or resist movement of at least one component part relative to at least one other component part; and
   control means in communication with the movement sensing means and the movement resisting means, the control means being programmed to interpret and/or analyze the said one or more output signals generated by said movement sensing means within predetermined parameters and/or criteria;
wherein one or more of the movement resisting means are dynamically controlled in response to one or more signals being received from the control means when the control means determines a movement or change in movement requires partial or substantial immobilization of at least a portion of the spine of the wearer.

2. The brace device according to claim 1, wherein one or more of the component parts, alone or in combination with other component parts, are operable to substantially or partially encircle and/or lie adjacent to one or more portions of the spine of the wearer.

3. The brace device according to claim 2, wherein the one or more component parts are adapted to be arranged around the cervical and/or thoracic portion of the spinal column of the wearer.

4. The brace device according to claim 1, wherein the movement sensing means are adapted to monitor linear, shear and/or rotational movement.

5. The brace device according to claim 1, wherein the movement resisting means are adapted to resist linear, shear and/or rotational movement.

6. The brace device according to claim 4, wherein the movement sensing means are adapted to sense the rate of change in velocity (acceleration and/or deceleration) and/or a change in inclination (pitch and/or yaw).

7. The brace device according to claim 6, wherein movement sensing means include one or more accelerometers, gyroscopes, force-transducers, pressure sensors and/or strain gauges.

8. The brace device according to claim 7, wherein the one or more accelerometers and/or gyroscopes are capable of detecting movement changes in three dimensions.

9. The brace device according to either claim 7 or 8, wherein the movement sensing means are micro electro-mechanical systems.

10. The brace device according to claim 1, wherein the movement sensing means are operable to provide signals and/or data relating to the severity of the physiological conditions applied to the wearer.

11. The brace device according to claim 1, wherein the movement sensing means are located on one or more component parts and on another part of the brace device.

12. The brace device according to claim 1, wherein the movement sensing means include the airbag deployment system and/or the dynamic stability control system of the vehicle in which the wearer is travelling.

13. The brace device according to claim 1, wherein the control means is an electronic microprocessor in communication with the movement sensing means and the movement resisting means.

14. The brace device according to claim 13, wherein the communication is wireless and/or through electrical conducting wires.

15. The brace device according to claim 1, wherein the component parts are operable to articulate, relative to one another, at one or more interfaces defined by the movement resisting means, whereby a tendency for a motion of one component part relative to another component part is prohibited, restricted and/or resisted.

16. The brace device according to claim 15, wherein a tendency for the component parts to remain in a statically abnormal immobilization configuration after receiving signals from the control means, or to urge further secondary movement between the component parts into a secondary immobilization configuration, may be permanently or temporarily assisted to prevent or mitigate further injury from rebound or recoil movement of the head and/or body of the wearer after a potentially injurious event.

17. The brace device according to claim 1, wherein the component parts are adapted from moveable, overlapping plates.

18. The brace device according to claim 17, wherein the movement resisting means are typically located in the region of possible overlap.

19. The brace device according to claim 18, wherein the movement resisting means are electromagnetic lock assemblies.

20. The brace device according to claim 18, wherein the movement resisting means are mechanical, electrical, magnetic and/or chemical locking mechanisms.

21. The brace device according to claim 1, wherein means for generating a wireless distress signal are provided, operable to be generated after the activation of the brace device.

22. The brace device according to claim 1, wherein one or more component parts are connected to a helmet worn by the wearer.

23. The brace device according to claim 22, wherein the helmet itself be formed of one or more parts, at least one of which is operable to function in combination with one or more component parts of the brace device.

24. The brace device according to claim 1, wherein vertical translational movement is restricted or resisted to a greater extent than lateral movement.

25. A brace device for the spinal support of a wearer, the brace device comprising:
   a flexible smart fabric, operable to partially or substantially enclose and/or lie adjacent to one or more portions of the spine of the wearer;
   movement sensing means, for monitoring the movement of at least one location on the smart fabric relative to one or more other locations on the smart fabric and/or other portions of the brace device, the movement sensing means generating one or more output signals indicative of said movement or in response to a change in movement;
   fabric hardening means, operable to partially or substantially harden one or more regions of the smart fabric upon application of a stimulus, thereby to prohibit, restrict and/or resist movement of one or more portions of the spine of the wearer; and
   control means in communication with the movement sensing means and the hardening means, the control means being programmed to interpret and/or analyze the said one or more output signals generated by said movement sensing means within predetermined parameters and/or criteria;
wherein one or more regions of the flexible fabric is dynamically controlled in response to one or more signals being received from the control means when the control means determines a movement or change in movement requires support of the spine of the wearer.

26. The brace device according to claim 25, wherein the smart fabric is connected to a helmet worn by the wearer.

27. The brace device according to claim 26, wherein the helmet may itself incorporate a smart fabric which may respond independently and/or in response to one or more signals being received from the control means.

28. The brace device according to claim 25, wherein the hardening means and/or the applied stimulus may be thermal, chemical, mechanical, electrical or magnetic.

29. The brace device according to either claim 1 or claim 25, wherein the brace device further comprises sensors for monitoring the physical condition or the wearer.

30. The brace device according to claim 29, wherein the sensors monitor the heart rate, body temperature, blood pressure and/or the presence and/or location of bleeding.

31. A brace device for the support of a wearer, the brace device comprising:
   a flexible smart fabric, operable to partially or substantially enclose and/or lie adjacent to one or more portions of the muscular-skeletal system of the wearer;
   movement sensing means, for monitoring the movement of at least one location on the smart fabric relative to one or more other locations on the smart fabric and/or other portions of the brace device, the movement sensing means generating one or more output signals indicative of said movement or in response to a change in movement;
   fabric hardening means, operable to partially or substantially harden one or more regions of the smart fabric upon application of a stimulus, thereby to prohibit, restrict and/or resist movement of one or more portions of the muscular-skeletal system of the wearer; and
   control means in communication with the movement sensing means and the hardening means, the control means being programmed to interpret and/or analyze the said one or more output signals generated by said movement sensing means within predetermined parameters and/or criteria;
wherein one or more regions of the flexible fabric is dynamically controlled in response to one or more signals being received from the control means when the control means determines a movement or change in movement requires support of the muscular-skeletal system of the wearer.

32. The brace device according to either claim 1 or 25, wherein the dynamic control is operable to reactivate and/or vary the duration and/or force applied by the movement resisting means in prohibiting, restricting and/or resisting movement.

33. The brace device according to claim 31, wherein the dynamic control is operable to reactivate and/or vary the duration and/or force applied by the fabric hardening means in prohibiting, restricting and/or resisting movement.

* * * * *